(12) United States Patent
Tseng et al.

(10) Patent No.: US 7,943,117 B2
(45) Date of Patent: May 17, 2011

(54) METHOD FOR TESTING RADIOCHEMICAL PURITY OF TC-99M-TRODAT-1

(75) Inventors: Yu-Chin Tseng, Pingjhen (TW); Yuen-Han Yeh, Jhunan Township, Miaoli County (TW); Mei-Chih Wu, Sansia Township, Taipei County (TW); Lie-Hang Shen, Jhongli (TW)

(73) Assignee: Atomic Energy Council—Institute of Nuclear Research, Taoyuan (TW)

( * ) Notice: Subject to any disclaimer, the term of this patent is extended or adjusted under 35 U.S.C. 154(b) by 1173 days.

(21) Appl. No.: 11/448,882

(22) Filed: Jun. 8, 2006

(65) Prior Publication Data
US 2007/0286802 A1    Dec. 13, 2007

(51) Int. Cl.
*A61K 51/00* (2006.01)
*A61M 36/14* (2006.01)
(52) U.S. Cl. .................................... 424/1.65; 424/1.11
(58) Field of Classification Search ................. 424/1.11, 424/1.65
See application file for complete search history.

(56) References Cited

U.S. PATENT DOCUMENTS 5,690,904 A * 11/1997 MacWhorter et al. ....... 424/1.65
6,241,963 B1 * 6/2001 Kung et al. .................. 424/1.65
7,597,875 B2 * 10/2009 Archer et al. ................ 424/1.65

OTHER PUBLICATIONS

Shabir, G. "HPLC Method Development and Validation for Pharmaceutical Analysis," PharmTec.com, Mar. 2004.*
Snyder et al., Practical HPLC Method Development, 1997.*
Luyt et al., Bioconjugate Chem., 1999, 10, p. 470-479.*
Center for Drug Evaluation and Research, Reviewer Guidance Validation of Chromatographic Methods, 1994, p. 1-29.*

* cited by examiner

*Primary Examiner* — Michael G Hartley
*Assistant Examiner* — Leah Schlientz
(74) *Attorney, Agent, or Firm* — Jackson IPG PLLC; Demian K. Jackson (57) ABSTRACT

The present invention is to invent a novel method for testing the radiochemical purity of Tc-99m-TRODAT-1 through a high performance liquid chromatography on a widely available C-18 column.

9 Claims, 11 Drawing Sheets

| Test No. | Resolution (Rs) of the first peak of Tc-99m-TRODAT-1 to impurity (n=6) | Resolution of the second peak of Tc-99m-TRODAT-1 to impurity (n=6) | Qualified? |
|---|---|---|---|
| 1 | 11.523 | 4.654 | Qualified when Rs>1.5 |
| 2 | 12.531 | 4.475 | |
| 3 | 14.308 | 4.564 | |
| 4 | 11.100 | 5.023 | |
| 5 | 10.153 | 4.524 | |
| 6 | 9.125 | 4.423 | |
| Average | 11.457 | 4.611 | |

| The theoretical RCP of sample | Recovery (%) | | | |
|---|---|---|---|---|
| | First test | First test | First test | First test |
| 95% | 100.3% | 100.9% | 102.0% | 101.07% |
| 90% | 97.7% | 99.7% | 98.5% | 98.63% |
| 80% | 96.6% | 97.7% | 96.8% | 97.03% |
| 70% | 96.5% | 97.3% | 98.1% | 97.30% |
| 60% | 91.8% | 94.5% | 95.8% | 94.03% |
| 50% | 88.5% | 92.4% | 85.7% | 88.87% |
| CV(%) | 4.50% | 3.26% | 5.76% | 4.51% |
| Correlation | 0.999 | 1.000 | 0.997 | 0.999 |

FIG. 5

| DMGA pH value | pH=7.0 | pH=6.5 | pH=7.5 | pH=7.0 | pH=6.5 | pH=7.5 | pH=7.0 | pH=6.5 | pH=7.5 |
|---|---|---|---|---|---|---|---|---|---|
| Composition of eluent | ACN/DMGA=60/40 ||||||||||
| Equipment | PerkinElmer HPLC equipment ||||||||||
| Test No. | Retention time of first Tc-99m-TRODAT-1 (min) ||| Retention time of first Tc-99m-TRODAT-1 (min) ||| Resolution (Rs) of first Tc-99m-TRODAT-1 to impurity |||
| 1 | 22.75 | 22.53 | 23.23 | | | | 11.523 | 10.524 | 11.480 |
| 2 | 22.81 | 22.50 | 23.19 | | | | 12.531 | 12.323 | 11.99 |
| 3 | 22.77 | 22.48 | 23.24 | | | | 14.308 | 11.933 | 10.745 |
| Average | 22.78 | 22.50 | 23.22 | | | | 12.787 | 11.593 | 11.405 |
| Standard Deviation | 0.031 | 0.025 | 0.026 | | | | Qualified? (Rs>1.5) ☑Yes ☐No |||
| CV%(n=3) | 0.13% | 0.11% | 0.11% | | | | |||
| Average | 22.83 ||||||||||
| Standard Deviation | 0.314 ||||||||||
| CV%(n=9) | 1.38% ||||||||||

FIG.6A

| DMGA pH value | pH=7.0 | pH=6.5 | pH=7.5 | pH=7.0 | pH=6.5 | pH=7.5 |
|---|---|---|---|---|---|---|
| Composition of eluent | ACN/DMGA=60/40 | | | | | |
| Equipment | PerkinElmer HPLC equipment | | | | | |
| Test No. | Retention time of second Tc-99m-TRODAT-1 (min) | | | Resolution (Rs) of second Tc-99m-TRODAT-1 to impurity | | |
| 1 | 24.36 | 24.22 | 24.79 | 4.654 | 2.385 | 4.802 |
| 2 | 24.36 | 24.11 | 24.82 | 4.475 | 5.018 | 4.734 |
| 3 | 24.36 | 24.16 | 24.73 | 4.564 | 4.669 | 4.386 |
| Average | 24.36 | 24.16 | 24.78 | 4.564 | 4.024 | 4.641 |
| Standard Deviation | 0.000 | 0.055 | 0.046 | | Qualified?(Rs>1.5) | |
| CV%(n=3) | 0.00% | 0.23% | 0.18% | | ☑Yes ☐No | |
| Average | 24.43 | | | | | |
| Standard Deviation | 0.275 | | | | | |
| CV%(n=9) | 1.13% | | | | | |

FIG.6B

| Composition of eluent | ACN/DMGA =60/40 | ACN/DMGA =63/37 | ACN/DMGA =57/43 | ACN/DMGA =60/40 | ACN/DMGA =63/37 | ACN/DMGA =57/43 |
|---|---|---|---|---|---|---|
| Equipment | \multicolumn{6}{l|}{Waters HPLC equipment  DMGA pH=7.0} |
| Test No. | \multicolumn{3}{l|}{Retention time of first Tc-99m-TRODAT-1 (min)} | \multicolumn{3}{l|}{Resolution (Rs) of first Tc-99m-TRODAT-1 to impurity} |
| 1 | 24.053 | 18.883 | 29.273 | 19.727 | 14.412 | 26.581 |
| 2 | 24.080 | 19.003 | 29.300 | 24.316 | 16.146 | 25.435 |
| 3 | 24.107 | 19.027 | 29.327 | 21.467 | 18.764 | 31.108 |
| Average | 24.080 | 18.971 | 29.300 | 21.837 | 16.441 | 27.708 |
| Standard Deviation | 0.027 | 0.077 | 0.027 | | | |
| CV%(n=3) | 0.11% | 0.41% | 0.09% | | | |
| Average | \multicolumn{3}{l|}{24.117} | | | |
| Standard Deviation | \multicolumn{3}{l|}{4.473} | \multicolumn{3}{l|}{Qualified? (Rs>1.5) ☑Yes ☐No} |
| CV%(n=9) | \multicolumn{3}{l|}{18.55%} | | | |

FIG.6C

| Composition of eluent | ACN/DMGA =60/40 | ACN/DMGA =63/37 | ACN/DMGA =57/43 | ACN/DMGA =60/40 | ACN/DMGA =63/37 | ACN/DMGA =57/43 |
|---|---|---|---|---|---|---|
| Equipment | DMGA pH=7.0 Waters HPLC equipment ||||||
| Test No. | Retention time of second Tc-99m-TRODAT-1 (min) ||| Resolution (Rs) of second Tc-99m-TRODAT-1 to impurity |||
| 1 | 25.757 | 20.083 | 31.573 | 8.246 | 6.575 | 9.761 |
| 2 | 25.783 | 20.200 | 31.590 | 8.614 | 6.411 | 9.751 |
| 3 | 25.807 | 20.243 | 31.627 | 8.390 | 6.362 | 10.467 |
| Average | 25.782 | 20.175 | 31.597 | 8.417 | 6.449 | 9.993 |
| Standard Deviation | 0.025 | 0.083 | 0.028 | | | |
| CV%(n=3) | 0.10% | 0.41% | 0.09% | | | |
| Average | 25.851 |||||| 
| Standard Deviation | 4.946 |||||| 
| CV%(n=9) | 19.13% |||||| 
| | | | | Qualified?(Rs>1.5) ☑Yes ☐No |||

METHOD FOR TESTING RADIOCHEMICAL PURITY OF TC-99M-TRODAT-1

FIELD OF THE INVENTION

The present invention relates to a radiochemical purity testing method; more particularly, relates to a method for measurement of radio chemical purity of Tc-99m-TRODAT-1 through a high performance liquid chromatography (HPLC) on a widely available C-18 column.

DESCRIPTION OF THE RELATED ART

All radioactive medicinal products should be assayed for radioactive content prior to administration. A prior art of radiochemical purity test for Tc-99m-TRODAT-1 was invented by Dr. Hank F. Kung. The radio labeling mixtures of a kit within TRODAT-1, Tc-99m-TRODAT-1 and other impurities, were purified by a HPLC equipped with radiodetector on a PRP-1 column (250×4.1 mm) using acetonitrile/3,3-dimethyl glutaric acid (DMGA) buffer (5 mM, pH=7) 82:20 as the eluent at a flow rate of 1.0 mL/min.

Figure 7:
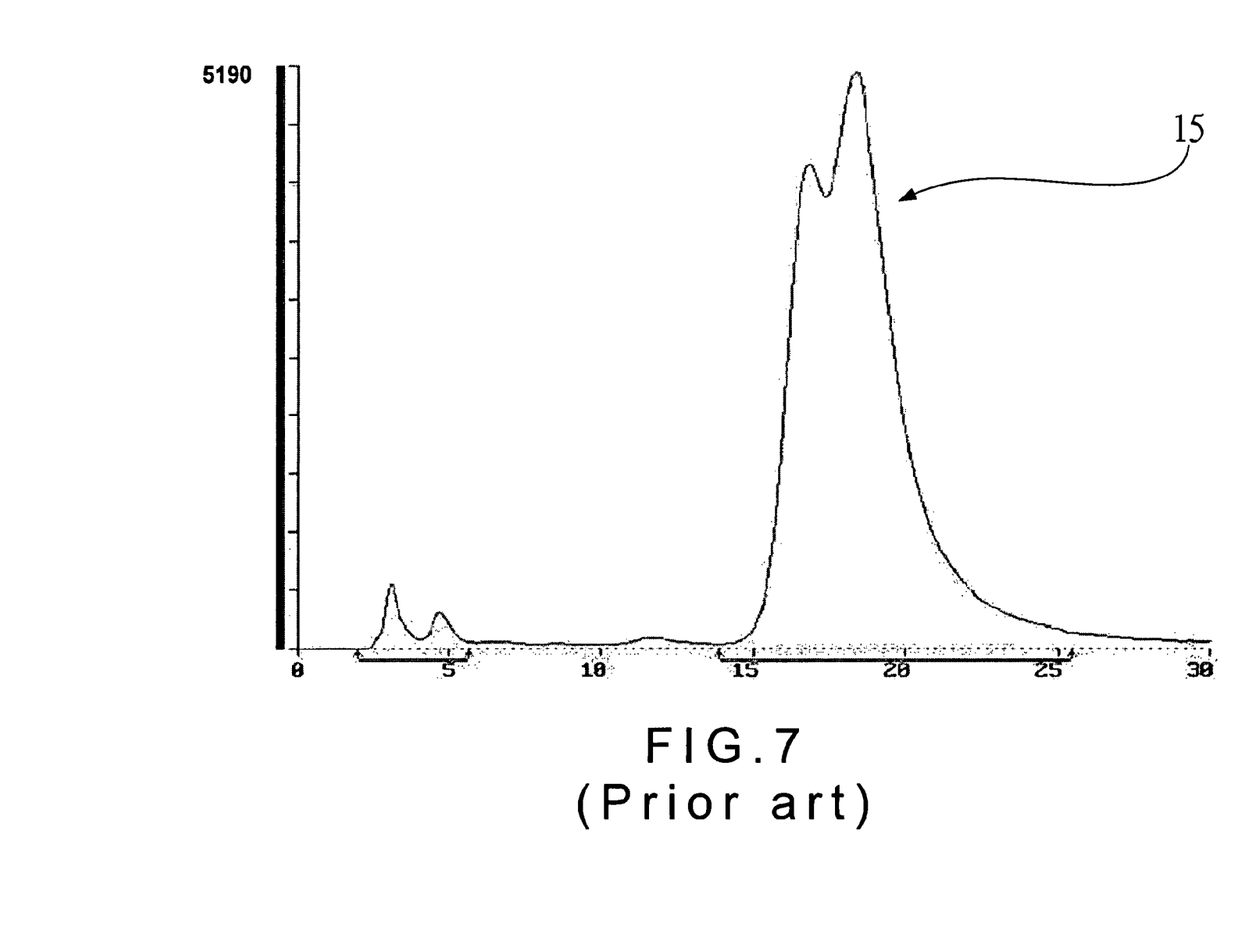
FIG. 7 is a chromatography view of the prior art.

The chromatography obtained through the above method is shown in FIG. 7. Two major peaks corresponding to Tc-99m-TRODAT-1 [15] emerge in the elution profile due to TRO-DAT-1 forms at least two diasterisomers after chelating with a technetium. Each isomer displays similar binding affinity toward do pa mine transporter with little difference of Ki value (J. Med Chem 1998, 41:428-436); therefore each component is capable of being exploited as an active substance without further separation.

The method invented by Dr. Kung has the following disadvantages: (1) The peak tailing of Tc-99m-TRODAT-1 is very obviously, causing poor resolution of Tc-99m-TRODAT-1 to impurity (Rs<1.5). (2) Some impurities may not be separated from active substance, leading to an overestimation of the radiochemical purity of Tc-99m-TRODAT-1. (3) Compared to C-18 column, PRP-1 column is not widespread available and its quality is not stable enough to ensure its application on radiochemical test. Hence, the prior art does not fulfill users' requests on routine application.

SUMMARY OF THE INVENTION

The main purpose of the present invention is to obtain a novel method for testing radiochemical purity of Tc-99m-TRODAT-1 with a widely available C-18 column.

The present invention consists of the following steps: reconstructing a kit with TRODAT-1 ingredient with Tc-99m pertechnetate solution for obtaining Tc-99m-TRODAT-1 solution as a sample; delivering an eluent of a mixture of acetonitrile and 5 mM of DMGA of pH 7.0 into a C-18 column under a certain speed by using a high pressure pump; injecting an amount of sample into the C-18 column by using an injector; eluting the C-18 column with the eluent to process a separation of the sample to elute out comes from the C-18 column sequentially; and processing the C-18 column with a radiodetector to obtain a chromatography, where the detector is a radio-detector; and the C-18 column is a Waters Nova-Pack C-18 column or a Gemini C-18 column. Accordingly, a novel method for testing a radiochemical purity of Tc-99m-TRODAT-1 is obtained.

BRIEF DESCRIPTIONS OF THE DRAWINGS

The present invention would be better understood from the following detailed descriptions of the preferred embodiments according to the present invention, taken in conjunction with the accompanying drawings, in which.

DESCRIPTION OF THE PREFERRED EMBODIMENTS

The following descriptions of the preferred embodiments are provided to interpret the features and the structures of the present invention.

The present invention is a method for testing a radiochemical purity of Tc-99m-TRODAT-1, comprising the following steps:

(A) Reconstructing a kit within TRODAT-1 ingredient to obtain Tc-99m-TRODAT-1 solution as a sample.

(B) And a high performance liquid chromatography (HPLC) is used to process a radiochemical purity test to the sample. The HPLC testing method comprises the following steps:

(I) An eluent is delivered to a chromatography column at a certain speed by using a high pressure pump (II) An amount of the sample is injected into the chromatography column by using an injector.

(III) The chromatography column is eluted by the eluent to process a separation of the sample so that some outcomes are eluted from the chromatography column sequentially.

(V) In the end, the chromatography column is processed with a radiodetector to obtain a chromatography.

The present invention obtains the eluent by mixing acetonitrile and 5 millimolars (mM) of 3,3-dimethylglutaric acid (DMGA) with pH value of 7.0. The eluent is delivered to the chromatography column at a speed between 0.5 milliliters per minute (ml/min) and 3 ml/min. The chromatography column is a C-18 column of a Waters Nova-Pack C-18 column (60 Å, 4 µM, 3.9 mm×150 mm; A stands for angstrom, µM for micrometer, and mm for millimeter) or a Gemini C-18 column (110 Å, 5 µM, 4.6 mm×250 mm). The sample is injected into the C-18 column in an amount between 0.5 microliters (µl) and 3 µl. And the detector is a radio-detector.

Figure 1:
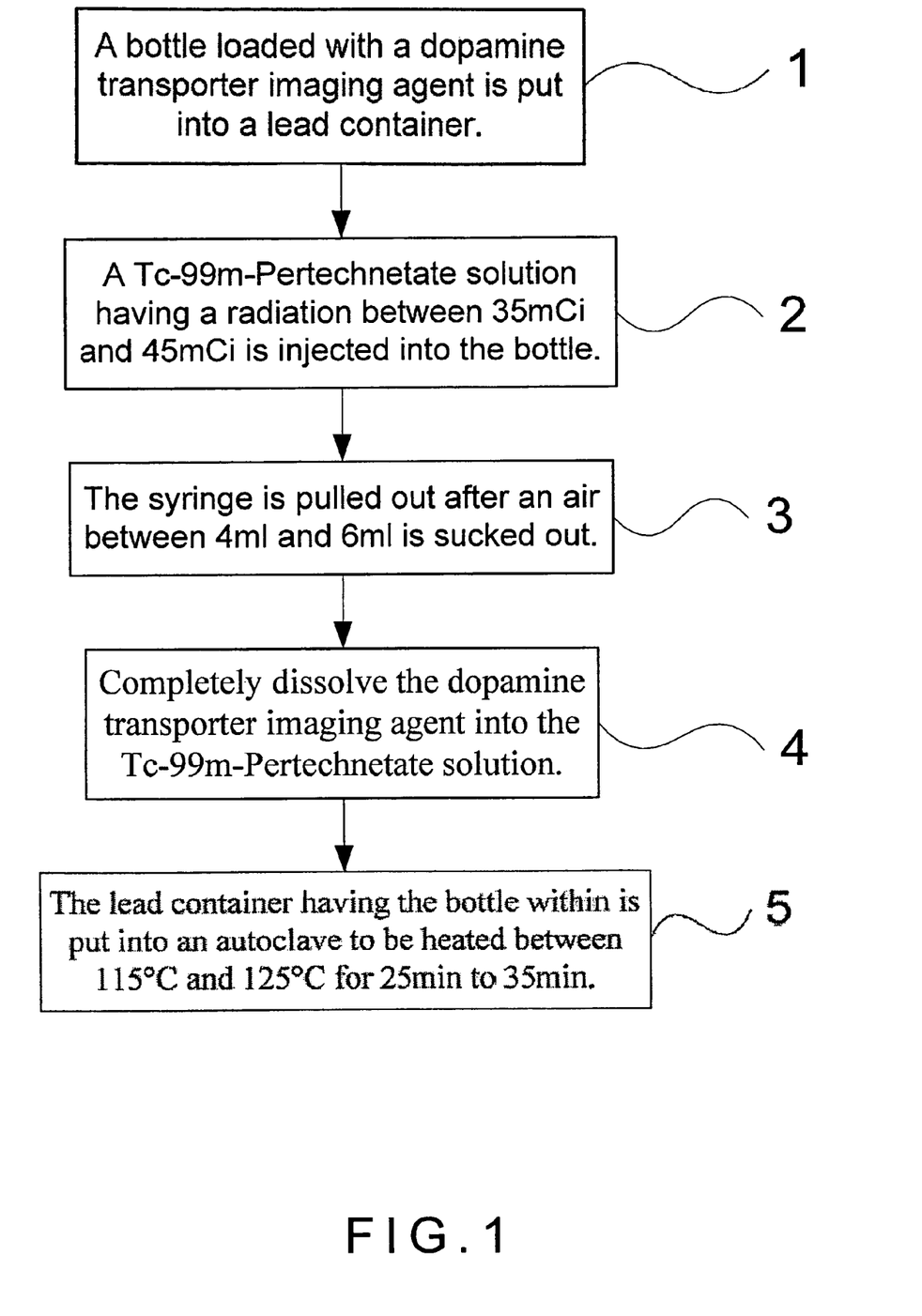
FIG. 1 is a view showing the process flow for reconstructing a kit with in TRODAT-1 ingredient to obtain Tc-99m-TRODAT-1 solution according to the present invention.

Please refer to FIG. 1, which is a view showing the process flow for reconstructing a kit within TRODAT-1 ingredient to obtain Tc-99m-TRODAT-1 solution according to the present invention. As shown in the figure, the Tc-99m-TRODAT-1 solution is obtained through the following steps:

Step (A) [1]: A TRODAT-1 kit vial is placed in a suitable lead container.

Step (B) [2]: Tc-99m-Pertechnetate solution with radioactivity between 35 millicuries (mCi) and 45 mCi is injected into the vial using a syringe, where the Tc-99m-Pertechnetate solution is diluted with a sodium chloride solution of a concentration between 0.85 percents (%) and 0.95%

Step (C) [3]: The syringe is pulled out after an amount of air between 4 milliliters (ml) and 6 ml is withdrawn out.

Step (D) [4]: The lead vial is shaken for 5 seconds to 15 seconds to ensure complete dissolution of the contents.

Step (E) [5]: Finally, the lead vial is put into an autoclave to be heated between 115 Celsius degrees (° C.) and 125° C. for 25 minutes (min) to 35 min, then cooling down the lead vial to room temperature to obtain the sample for an analysis.

The following preferred embodiments use Gemini C-18 columns as chromatography column for radiochemical purity test of Tc-99m-TRODAT-1. The radiochemical purity test comprises the following steps: (A) A Tc-99m-TRODAT-1 solution is obtained as a sample. (B) And, the sample is processed through the radiochemical purity test by using a high performance liquid chromatography (HPLC). The HPLC in step (B) comprises the following steps: (I) An eluent is delivered to a Gemini C-18 column by using a high pressure pump at a speed of 1 ml/min. The eluent is obtained by mixing an acetonitrile and 5 mM of DMGA. (II) 1 μl of the sample is injected into the Gemini C-18 column by an injector. (III) The Gemini C-18 column is eluted by the eluent to process a separation of the sample so that some outcomes are eluted from the Gemini C-18 column sequentially. (IV) Consequently, a radio-detector is used to transform the changing of the outcomes into electrical signals to be amplified for obtaining a chromatography. Therein, the mixing volume of the acetonitrile to the 5 mM of DMGA is 60 to 40 (60/40).

Figure 2:
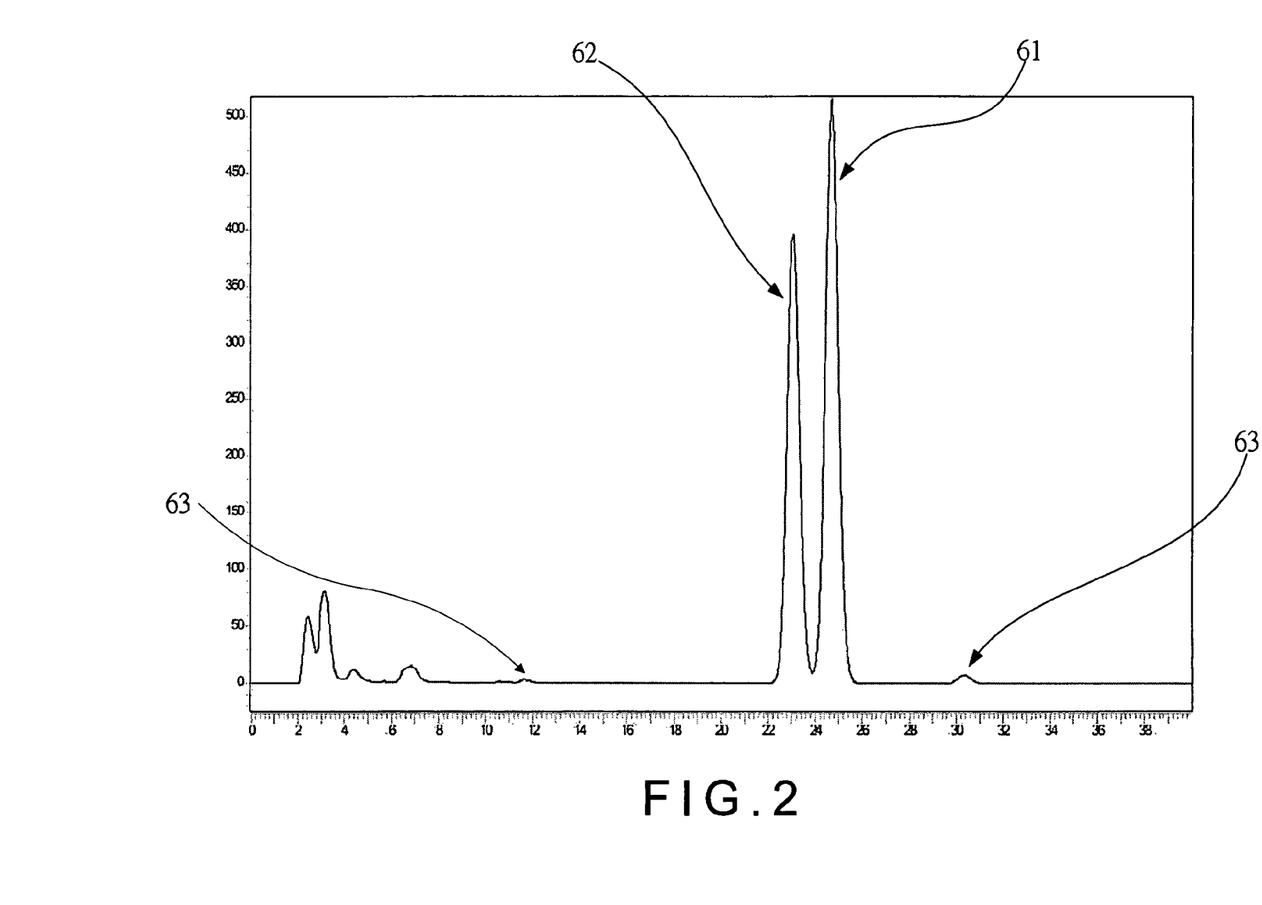
FIG. 2 is a view of the chromatography.

Please refer to FIG. 2, which is a view of the chromatography. In the figure, the first peak of Tc-99m-TRODAT-1 [61], the second peak of Tc-99m-TRODAT-1 [62] and the profile of impurities [63] are shown. Hence, according to the present invention, the Tc-99m-TRODAT-1 shows the first peak of Tc-99m-TRODAT-1 [61] and the second peak of Tc-99m-TRODAT-1 [62] separately, where it is evidently that there are at least two diasterisomers of Tc-99m-TRODAT-1, and both are capable of binding toward dopamine transporter. On the other hand, it is also obviously that the Tc-99m-TRODAT-1 is well separated from the impurities, where the resolution (Rs) of a first Tc-99m-TRODAT-1 to the impurity is 11.548 and that of a second Tc-99m-TRODAT-1 to the impurity is 4.854, both greater than an ideal value (Rs>1.5). Regarding symmetry of the peaks, the tailing coefficients for the first Tc-99m-TRODAT-1 and the second Tc-99m-TRODAT-1 are 1.213 and 1.043 respectively, both lied within an ideal range (0.9~1.3).

The validation characteristics being considered for this analytical procedure are specificity, precision, linearity, accuracy, and robustness. Hence the test results obtained through the present invention are ensured and qualified.

Figure 3:
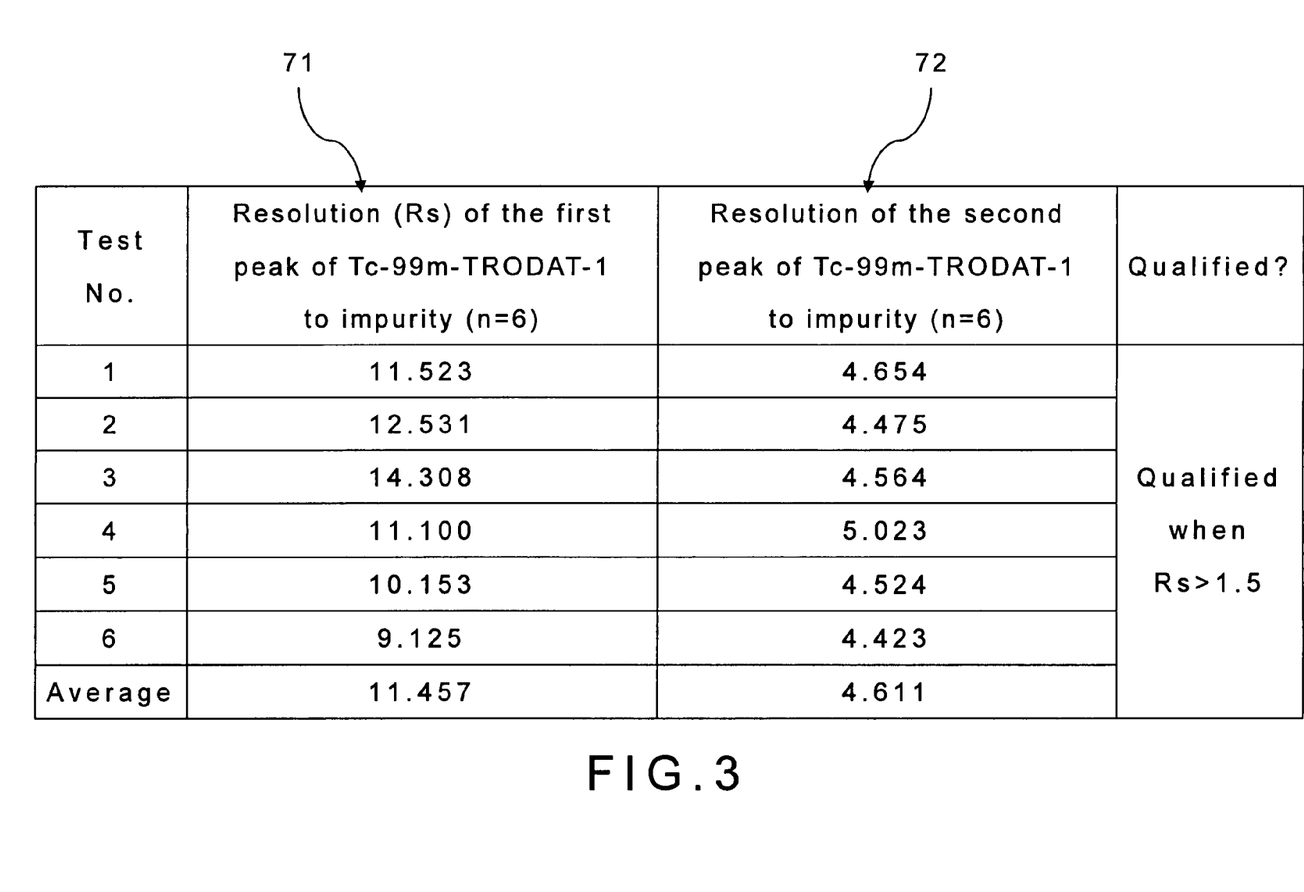
FIG. 3 is a view showing the analytical procedure validation of specificity.

Please refer to FIG. 3, which is a view showing the analytical procedure validation of specificity. The validation results obtained concerning the specificity of the analytical procedure, as shown in FIG. 3, are as follows: the average resolution of the first peak of Tc-99m-TRODAT-1 to the impurity [71] is 11.457; and the average resolution of the second peak of Tc-99m-TRODAT-1 to the impurity [71] is 4.611. Compared to prior art, Tc-99m-TRODAT-1 is well separated by the impurities according to the resolution obtained.

Figure 4A:
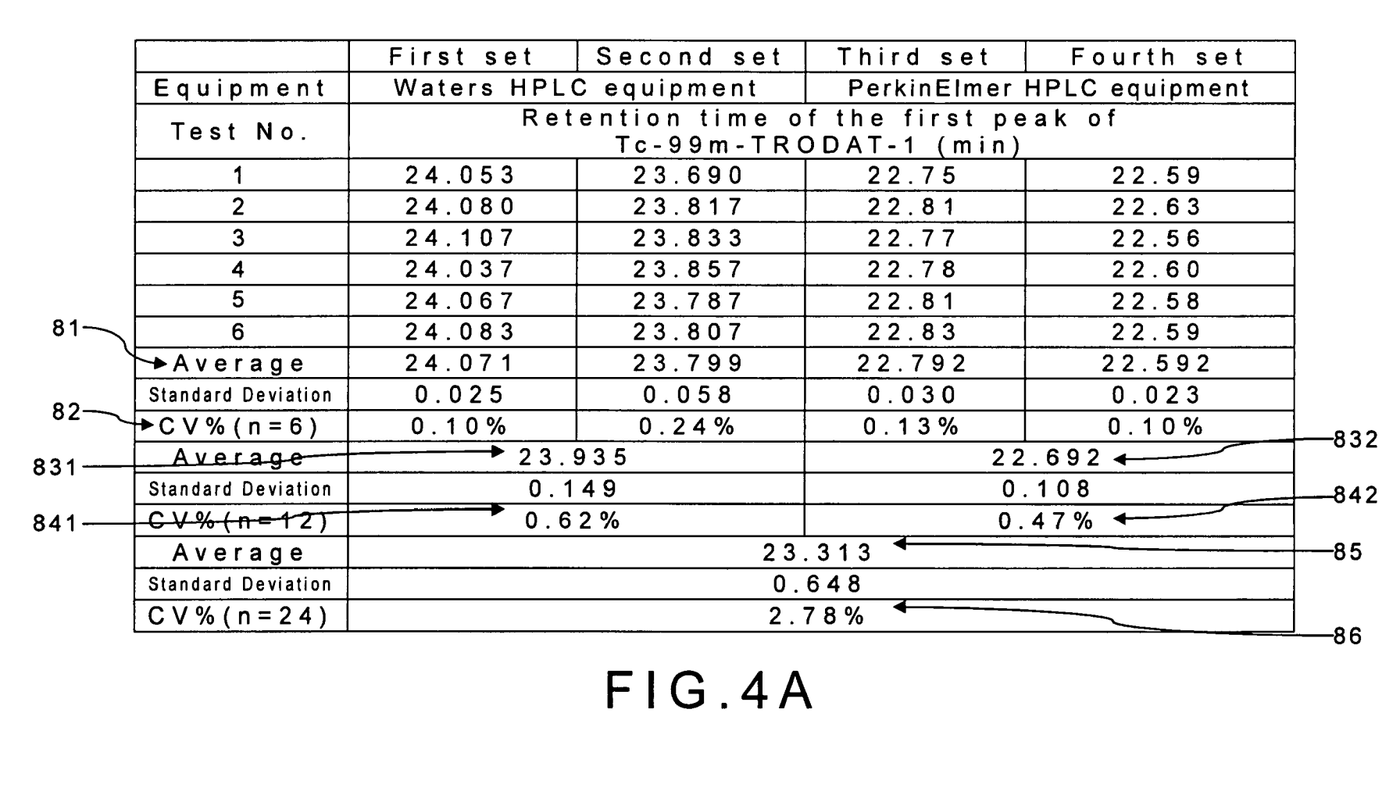
FIG. 4A is a view showing the analytical procedure validation of precision for the first peak of Tc-99m-TRODAT-1.
Figure 4B:
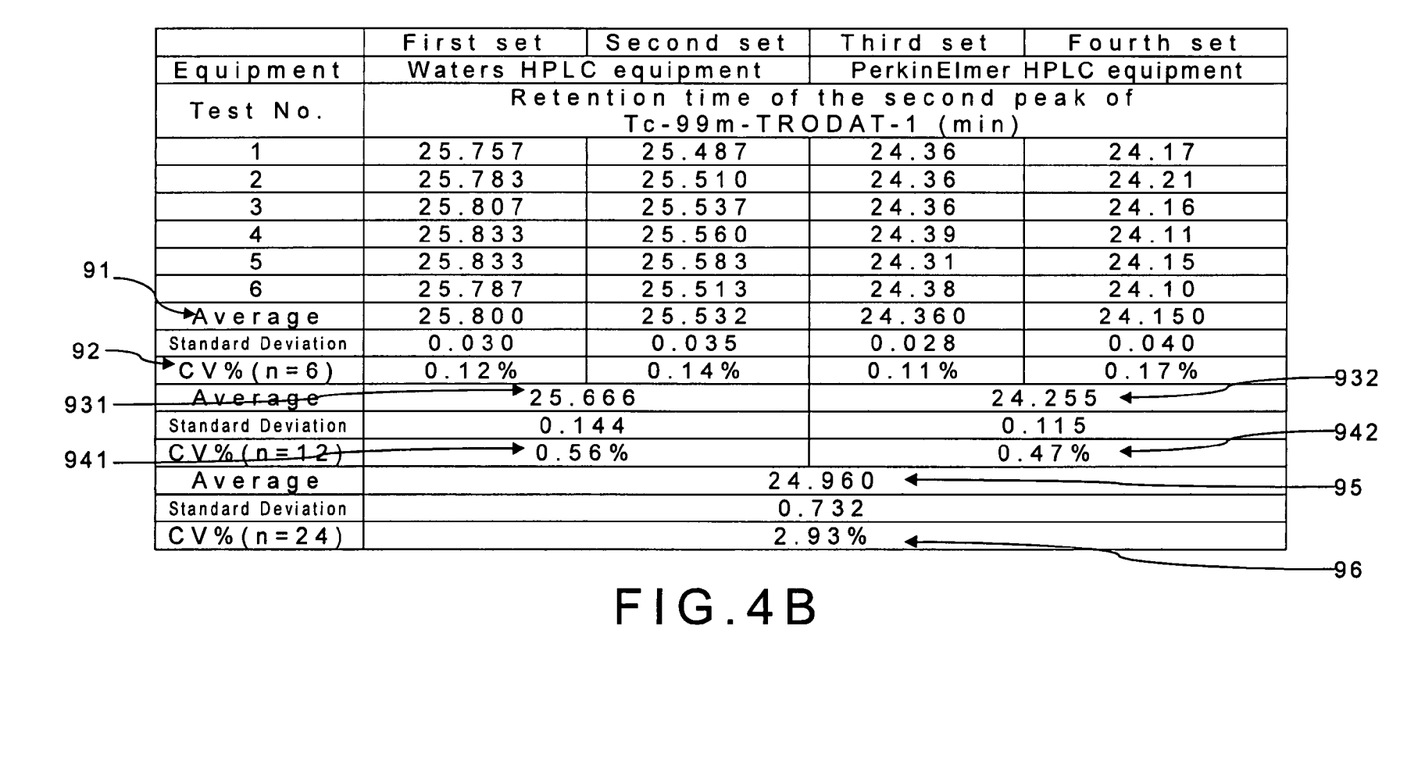
FIG. 4B is a view showing the analytical procedure validation of precision for the second peak of Tc-99m-TRODAT-1.

Please refer to FIG. 4A and FIG. 4B, which are views showing the analytical procedure validation of precision for the first and the second peak of Tc-99m-TRODAT-1. As shown in figures, the analytical procedure validation of precision is performed repeatability and intermediate precision for the retention time of Tc-99m-TRODAT-1. Regarding repeatability precision, the average retention times [81] of the first Tc-99m-TRODAT-1 are 24.071 min, 23.799 min, 22.792 min and 22.592 min; the coefficients of variation (CV) [82] for retention time of the first Tc-99m-TRODAT-1 are 0.10%, 0.24%, 0.13% and 0.10%; the average retention times [91] of the second Tc-99m-TRODAT-1 are 25.800 min, 25.532 min, 24.360 min and 24.150 min; and the CVs [92] for retention time of the second Tc-99m-TRODAT-1 are 0.12%, 0.14%, 0.11% and 0.17%. The above results are all qualified (CV≦2).

Regarding the intermediate precision, two aspects are concerned:

(A) Through using the same equipment by different operators on different days, two sets of results are obtained and each set comprises 12 result data. The first set uses a Waters HPLC equipment to obtain the average retention time [831] of the first peak of Tc-99m-TRODAT-1 as 23.935 min; the CV of the average retention time [841] for the first peak of Tc-99m-TRODAT-1 as 0.62%; the average retention time [931] of the second peak of Tc-99m-TRODAT-1 as 25.666 min; and the CV of the average retention time [941] of the second peak of Tc-99m-TRODAT-1 as 0.56%. The second set uses a PerkinElmer HPLC equipment to obtain the average retention time [832] of the first peak of Tc-99m-TRODAT-1 as 22.692 min; the CV of the average retention time [842] of the first peak of Tc-99m-TRODAT-1 as 0.47%; the average retention time [932] of the second peak of Tc-99m-TRODAT-1 as 24.255 min; and the CV of the average retention time [942] of the second peak of Tc-99m-TRODAT-1 as 0.47%. The above results are all qualified (CV≦2).

(B) Through using different equipments by different operators on different days, 24 result data are obtained. The average retention time [85] of the first peak of Tc-99m-TRODAT-1 is 23.313 min; the CV of the average retention time [86] of the first peak of Tc-99m-TRODAT-1 is 2.78%; the average retention time [95] of the second peak of Tc-99m-TRODAT-1 is 24.960 min; and the CV of the average retention time [96] of the second peak of Tc-99m-TRODAT-1 is 2.93%. The above results are all qualified (CV≦5%). For precision test of retention time, both diasterisomers of Tc-99m-TRODA-1 displayed similar results. According to the above results, the precision of retention time of Tc-99m-TRODAT-1 is ensured.

Figure 5:
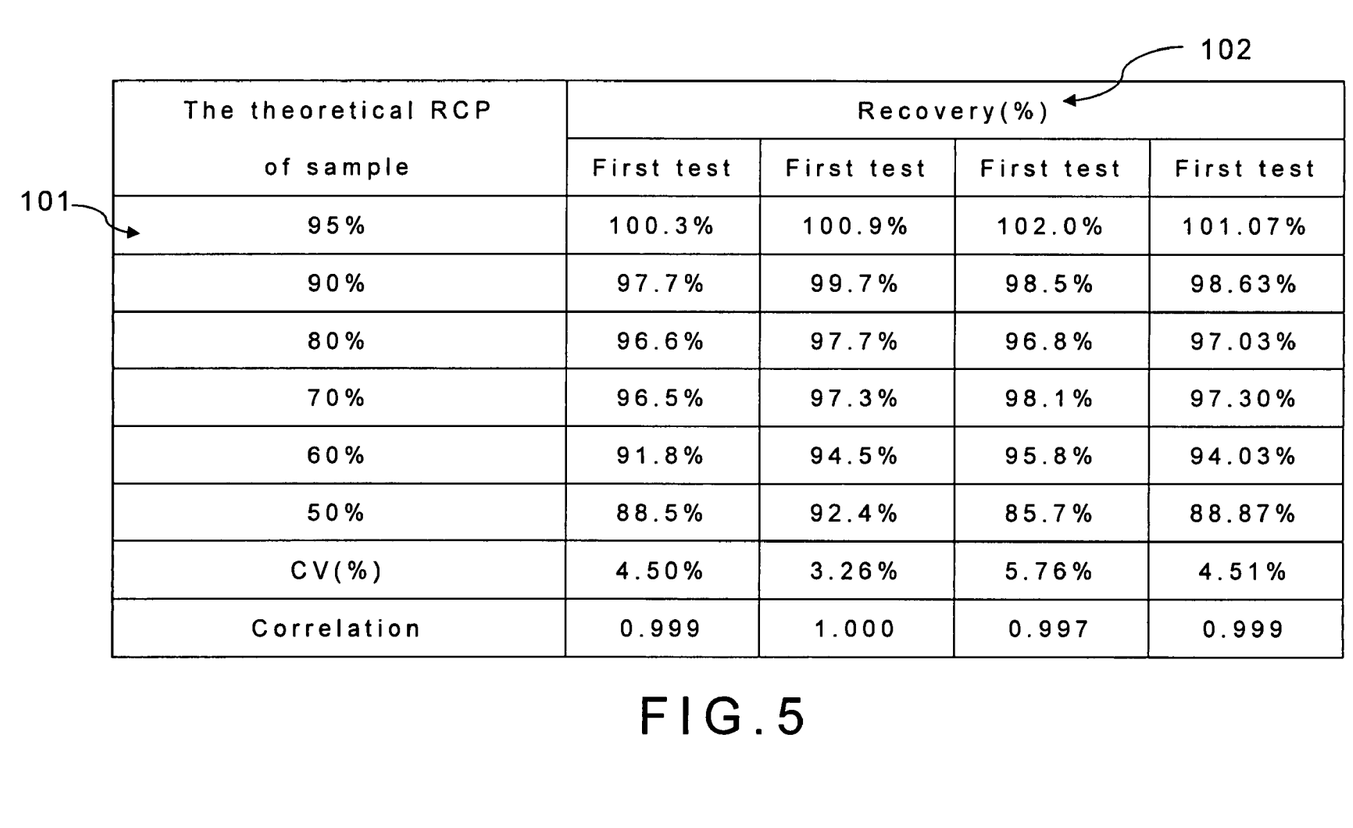
FIG. 5 is a view showing the analytical procedure validation of linearity and accuracy.

Please refer to FIG. 5, which is a view showing the analytical procedure validation of linearity and accuracy. As shown in the figure, the correlation between the actual radiochemical purity (RCP) of the Tc-99m-TRODAT-1 and a theoretical one are extremely high, where the correlation values are 0.999, 1.000 and 0.997 after three times of analysis and the average value is 0.999. The accuracy test measured a recovery of RCP [102] for each measuring range [101], where the values lies between 85.7% and 102.0% and are all qualified. The recovery values [102] of three accuracy tests have an average of 96.16% and a CV percentage of 4.51%. According to the above results, the analytical procedure validation of linearity and accuracy is qualified.

Figure 6A:
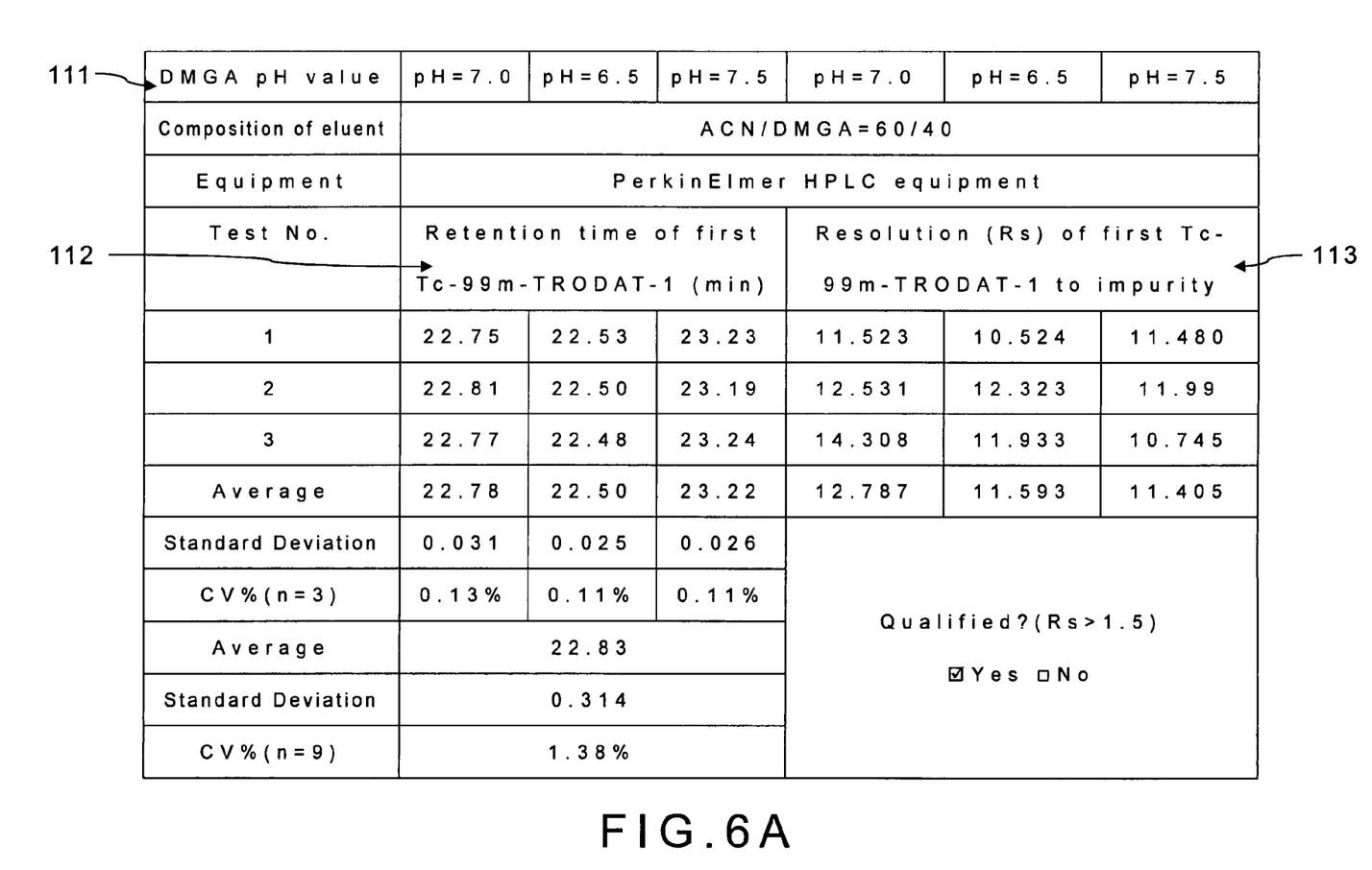
FIG. 6A is a view showing the analytical procedure validation of robustness on pH variation of mobile phase for the first peak of Tc-99m-TRODAT-1.
Figure 6B:
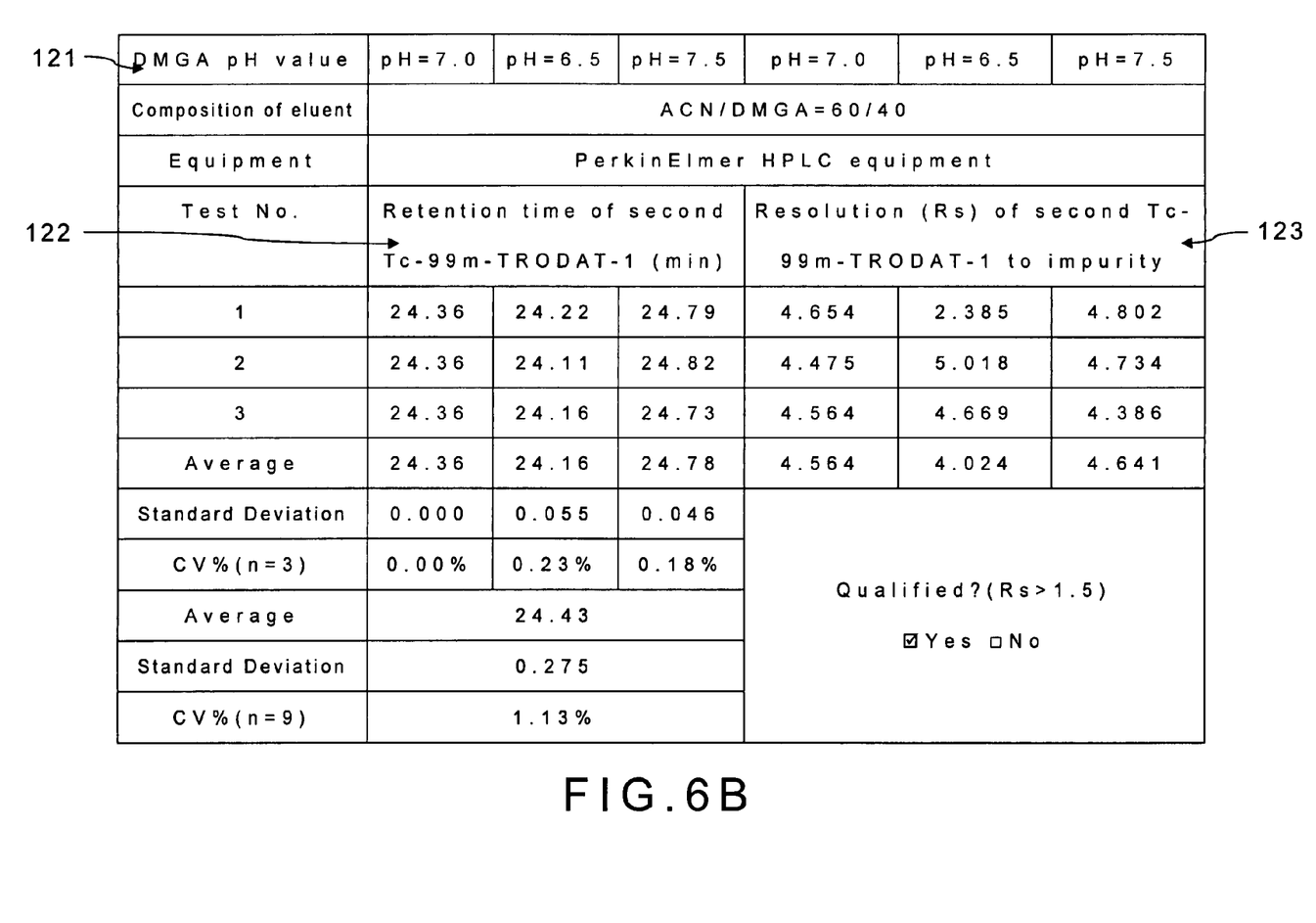
FIG. 6B is a view showing the analytical procedure validation of robustness on pH variation of mobile phase for the second peak of Tc-99m-TRODAT-1.

Please refer to FIG. 6A and FIG. 6B, which are views showing the analytical procedure validation of robustness on pH variation of mobile phase. As shown in the figures, the pH variation range [111, 121] of 5 mM of DMGA is between 6.5~7.5. The above results for robustness testing indicate the retention times [112, 122] as well as the resolution to impurities [113, 123] of the first and the second peak of Tc-99m-TRODAT-1 are not affected by the pH variation of 5 mM of DMGA buffer as the pH range [111, 112] between 6.5 and 7.5.

Figure 6C:
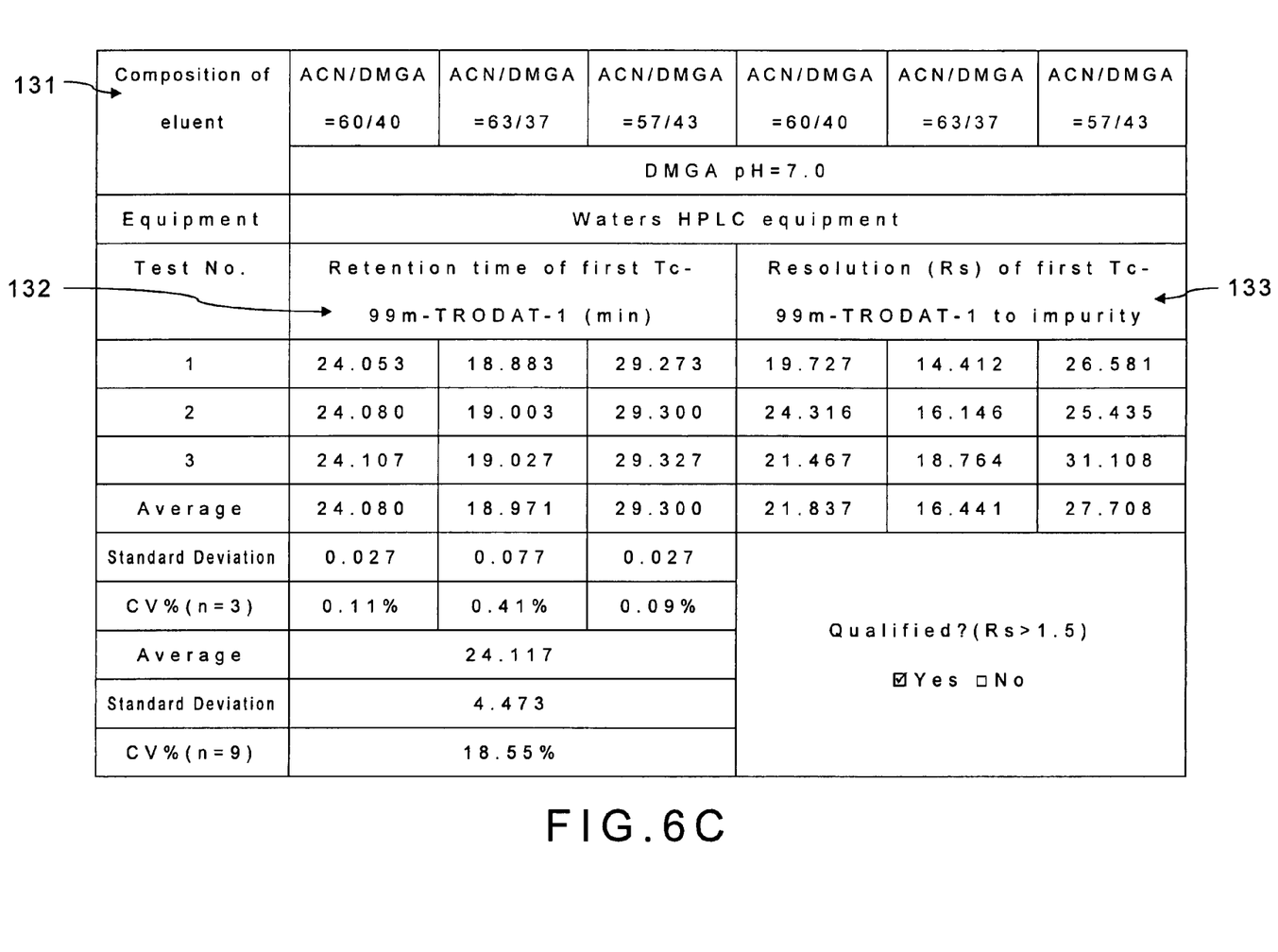
FIG. 6C is a view showing the analytical procedure validation of robustness on composition variation of mobile phase for the first peak of Tc-99m-TRODAT-1.
Figure 6D:
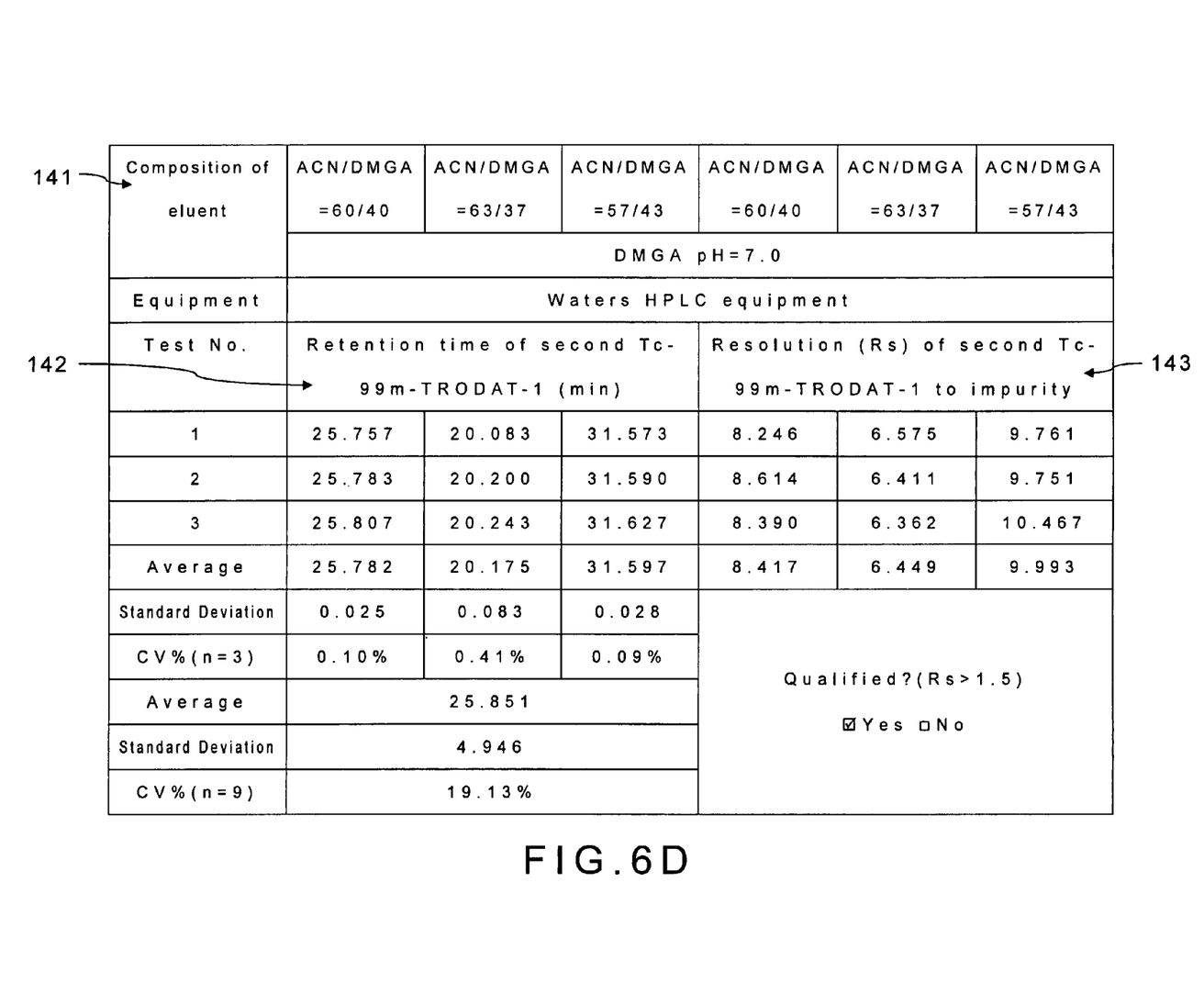
FIG. 6D is a view showing the analytical procedure validation of robustness on composition variation of mobile phase for the second peak of Tc-99m-TRODAT-1.

Please refer to FIG. 6C and FIG. 6D, which are views showing the analytical procedure validation of robustness on composition variation of mobile phase. As shown in the figures, the composition variation of mobile phase by changing the mixing volume [131, 141] of acetonitrile to 5 mM of DMGA, which are 60 to 40 (60/40), 63/37 and 57/43. As the results shows, the retention time of the first and the second peak of Tc-99m-TRODAT-[132, 142] shift significantly due to variation of composition variation of mobile phase. However, the resolution [132, 142] of the first and the second peak of Tc-99m-TRODAT-1 to impurities is still acceptable, indicating the robustness of composition variation of mobile phase is qualified.

To sum up, the present invention is a method for testing radiochemical purity of Tc-99m-TRODAT-1, where the method is validated to demonstrate that it is suitable for its intended purpose; and the C-18 column used is widely available with stable quality for the test.

The preferred embodiments herein disclosed are not intended to unnecessarily limit the scope of the invention. Therefore, simple modifications or variations belonging to the equivalent of the scope of the claims and the instructions disclosed herein for a patent are all within the scope of the present invention.

What is claimed is:

1. A method for testing radiochemical purity of Tc-99m-TRODAT-1, comprising steps of:
   (A) obtaining a Tc-99m-TRODAT-1 solution as a sample; and
   (B) processing an test through a high performance liquid chromatography (HPLC), said HPLC comprising steps of:
      (I) delivering an eluent into a chromatography column under a certain speed by using a high pressure pump;
      (II) injecting an amount of sample into said chromatography column by using an injector;
      (II) eluting said chromatography column by using said eluent to process a separation of said sample to elute outcomes from said chromatography column sequentially; and
      (IV) processing said chromatography column with a detector to obtain a chromatography,
   wherein said eluent is obtained by mixing acetonitrile and 5 millimolars of 3,3-dimethylglutaric acid (DMGA) with a pH value of 7;
   wherein said eluent is delivered to said chromatography column in a speed between 0.5 milliliters per minute (ml/min) and 3 ml/min;
   wherein said chromatography column is a C-18 column;
   wherein said sample is injected into said chromatography column in an amount between 0.5 microliters (μl and 3 μl; and
   wherein said detector is a radio-detector;
   wherein the said chromatography results in a separation of two diastereomer peaks;
      the resolution (Rs) of the first diastereomer peak to the impurity is 11.548, 11.523, 12.531, 12.787 14.308, 11.100, 10.153, 9.125, or 11.457; the resolution (Rs) of the second diastereomer peak to the impurity is 4.854, 4.654, 4.475, 4.564, 5.023, 4.524, 4.423, or 4.611;
      and the tailing coefficient for the first peak is 1.213 and the tailing coefficient for the second peak is 1.043.

2. A method for testing radiochemical purity of Tc-99m-Trodat-1, comprising a step of subjecting a sample of Tc-99m-Trodat-1 to a high performance liquid chromatography (HPLC);
   wherein the said chromatography is performed on a C-18 column;
   wherein the said chromatography results in a separation of two diastereomer peaks;
      the resolution (Rs) of the first diastereomer peak to the impurity is 11.548, 11.523, 12.531, 12.787 14.308, 11.100, 10.153, 9.125, or 11.457; the resolution (Rs) of the second diastereomer peak to the impurity is 4.854, 4.654, 4.475, 4.564, 5.023, 4.524, 4.423, or 4.61 1; and
   the tailing coefficient for the first peak is 1.213 and the tailing coefficient for the second peak is 1.043.

3. The method according to claim 2, wherein the chromatography is performed using a mixture of acetonitrile and 3,3-dimethylglutaric acid (DMGA) as an eluent.

4. The method according to claim 2, wherein the chromatography is performed using a mixture of acetonitrile and 3,3-dimethylglutaric acid (DMGA) as an eluent; and wherein the pH of the eluent is 7.

5. The method according to claim 1, wherein the eluent is delivered to the chromatography column in a speed between 0.5 milliliters per minute (ml/min) and 3 ml/min.

6. The method according to claim 2, wherein the said chromatography results in a separation of two diastereomer peaks; and
   the resolution (Rs) of the first diastereomer peak to the impurity is 11.457.

7. The method according to claim 2, wherein the said chromatography results in a separation of two diastereomer peaks; and
   the resolution (Rs) of the first diastereomer peak to the impurity is 11.548.

8. The method according to claim 2, wherein the said chromatography results in a separation of two diastereomer peaks; and
   the resolution (Rs) of the second diastereomer peak to the impurity is 4.611.

9. The method according to claim 2, wherein the said chromatography results in a separation of two diastereomer peaks; and
   the resolution (Rs) of the second diastereomer peak to the impurity is 4.854.

* * * * *